(12) United States Patent
Mohtadi

(10) Patent No.: US 7,531,111 B2
(45) Date of Patent: May 12, 2009

(54) COMPOSITION AND PROBE FOR DETECTION OF HYDROCARBON MIXTURES

(76) Inventor: Nabil J. Mohtadi, 413 Joan St., South Plainfield, NJ (US) 07080-4918

( * ) Notice: Subject to any disclaimer, the term of this patent is extended or adjusted under 35 U.S.C. 154(b) by 335 days.

(21) Appl. No.: 11/704,133

(22) Filed: Feb. 8, 2007

(65) Prior Publication Data

US 2008/0193885 A1   Aug. 14, 2008

(51) Int. Cl.
*G01N 33/22* (2006.01)
*G01N 33/26* (2006.01)

(52) U.S. Cl. .................. 252/408.1; 436/60; 436/166; 422/55

(58) Field of Classification Search ............ 436/39, 436/40, 60, 166; 252/408.1, 963; 73/73; 422/55, 57
See application file for complete search history.

(56) References Cited

U.S. PATENT DOCUMENTS

| | | | |
|---|---|---|---|
| 922,152 A | 5/1909 | Kent | |
| 1,602,741 A | 10/1926 | Beck | |
| 1,866,743 A | 7/1932 | Abbott | |
| 2,520,933 A | 9/1950 | Berger | |
| 4,578,357 A | 3/1986 | Melpolder | |
| 4,699,885 A * | 10/1987 | Melpolder et al. | 436/39 |
| 5,048,334 A | 9/1991 | Hampton et al. | |
| 5,518,024 A | 5/1996 | Weeks et al. | |
| 6,376,250 B1 | 4/2002 | Mohtadi | |
| 6,981,335 B1 | 1/2006 | Darden et al. | |

FOREIGN PATENT DOCUMENTS

| | | |
|---|---|---|
| GB | 2 082 326 A | 8/1981 |
| GB | 2 259 366 A | 8/1992 |

* cited by examiner

*Primary Examiner*—Sean E Conley
(74) *Attorney, Agent, or Firm*—Mandel & Peslak, LLC; Arthur M. Peslak, Esq.

(57) ABSTRACT

A visual indicating paste for detecting the level of hydrocarbons in a storage container is disclosed. The visual indicating paste is a physical mixture of a non-polar dye, a high molecular weight carrier, a whitening agent and a filler material.

10 Claims, No Drawings

COMPOSITION AND PROBE FOR DETECTION OF HYDROCARBON MIXTURES

FIELD OF THE INVENTION

The present invention is directed to the field of visual indicating pastes used to detect the presence, and particularly the level, of hydrocarbon mixtures such as gasoline, kerosene, jet fuel, diesel fuel, heating oil, or other fuel and petroleum fractions in storage tanks.

More particularly, the present invention is directed to a visual indicating paste composition, which undergoes a change in color upon contact with the petroleum products in storage tanks, delivery vehicles, distribution systems, and any other system for the same purpose.

The composition of the indicating paste of the present invention is particularly adapted for use in determining the product level and thereby the volume of product in product storage and transportation tanks by applying the paste to a gauge that is inserted into the tank. The paste will change color when contacted by the petroleum products and the level of product in the tank is determined therefrom.

OBJECT AND SUMMARY OF THE INVENTION

An object of the present invention is to provide a visual indicating paste, which will, upon contact with hydrocarbons (petroleum products), produce a clear detectable color change.

Another object of the invention is to provide a visual indicating paste for producing a sharp and distinct color change on a gauge to which the paste is applied upon contact with the product without bleeding.

Still another object of the invention is to provide a visual indicating paste with very low solubility in the petroleum product (does not dissolve in the product), long shelf life and good adhesion to a substrate to which it is applied in use.

Still another object is to provide a visual indicating paste which is user-friendly and environmentally sound.

DETAILED DESCRIPTION OF THE INVENTION

The present invention is directed to a visual indicating paste comprising a non-polar dye, certain powder minerals, and certain inorganic oxides mixed with hydrocarbons in a semisolid mixture. The paste of the present invention provides considerable improvement in effectiveness and quality over presently available pastes in producing a detectable color change upon contact with petroleum products. In addition, the visual indicating paste of the present invention does not change its consistency or dissolve when introduced into the petroleum products.

In formulating the composition of the present invention, a selected dye is mixed in a carrier comprising a semisolid mixture of hydrocarbons with a solid inorganic oxide and a mineral. Specifically, the paste is created by a physical blending process during which no chemical reactions occur.

The dyes employed in the composition of the present invention are solvent dyes, which are readily available from commercial sources. The dyes are soluble in organic solvents. Solvent dyes are used to color organic solvent, hydrocarbons, fuels, waxes, lubricants, plastics and other non-polar materials. Fuel dyes are one use of solvent dyes. Various colors of the dyes may be used in connection with the present invention. When the paste is contacted by the petroleum products, it will change color from a light shade to a dark shade based upon the different solubility of the dye into the carrier and the product to be gauged. The molecules of the dye are typically non-polar or with little polarity, and do not undergo ionization. In addition, they are insoluble in water. Red dyes include various diazo dyes, e.g. Solvent Red 19, Solvent Red 24, Solvent Red 149, Permalex Red 2B, Permalex Violet B, Sudan Orange, Sudan Red 380, Oil Red, Orcosolve Red. Anthraquinone dyes are used for green and blue shades and include Solvent Green 33, Permalex Green 5B, Permalex Blue AP, Solvent Blue 35 and Orcosolve Oil Blue. Representative dyes employable in the composition of the present invention include; solvent Red 19, solvent Red 24, Orcosolve Oil Blue, Solvent Red 19, Solvent Red 24, Permalex Red 2B, Sudan orange, Sudan Red 380, Oil Red and Orcosolve Red. The paste of the present invention exhibits a very sharp color contrast between the light/white and the very dark shade of the same color, depending on the dye used. It is important to have a sharp, clear color cut of color change when the paste composition is employed in an environment like a storage tank containing dirt, rust or other dark colored materials or debris. If desired, admixtures of red dyes may be employed in amounts ranging from about 1:10 to 10:1 by weight, to achieve different shades or color contrasts when the paste composition is employed in an environment requiring a certain color. The preferred dye is Orcosolve Oil Blue in a concentration preferably between 0.9 to 1.4% by weight. Those of ordinary skill in the art will recognize that any dye meeting the aforementioned specifications is employable in the compositions of the present invention.

The non-polar dye is first blended into the carrier. The higher the molecular weight of the carrier, the less solubility of the dye into it. A higher molecular weight of the carrier will produce a better color change of the finished paste composition when introduced into contact with the petroleum product to be measured. At this point, the mixture changes color to the color of the dye which is normally a dark shade. In the present invention, Orcosolve Oil Blue is used as the preferred dye.

As the vehicle for the paste composition of the present invention, there is employed a semisolid carrier, which is not readily leached by the hydrocarbon product. The semisolid carrier should be of proper viscosity for good paste consistency. Lard and/or tallow in any ratio can be used as carriers. However, the preferred carrier is a mixture of lard and/or tallow and petrolatum in the ratio of 5 to 1 lard/petrolatum, or petroleum jelly, as it is commonly known. When Petrolatum is added to the carrier mixture, the consistency of the final product at low temperature will be maintained. Petroleum jelly is a semi-solid mixture of hydrocarbons (methane series C16 to C32, and of the olefin series). It does not oxidize on exposure to the air, and is not readily acted on by chemical reagents. It is insoluble in water. It is soluble in chloroform, benzene, carbon disulphide and oil and oil of turpentine. It also dissolves in warm ether and in hot alcohol but it separates from the latter in flakes on cooling. Lard and/or tallow is an animal fat produced from rendering the fat portion of an animal. Lard and tallow were commonly used as cooking oil though their use in contemporary cuisine has diminished because of health concerns posed by saturated fat and cholesterol. Lard and tallow are still commonly used to manufacture soap. Usually, the carrier is employed in an amount within 53 to 55 percent by weight. The carrier mixture of lard and/or tallow and Petroleum jelly as the carrier provides the best results for the present invention due to the low solubility of the dye in it and due to the fact that both lard and Petroleum jelly dissolve in the mixture of hydrocarbons very slowly.

The inorganic oxide employed as a constituent of the visual indicator paste composition of the present invention is an insoluble oxide and is used in the mixture as a whitener, and filler. Next a whitening agent is added and the color of the mixture becomes a very light shade of the initial color of the dye depending upon the whitening power of the inorganic oxide. Examples of whitening materials are calcium carbonate, zinc oxides, talcum, certain types of bentonite and titanium oxide.

The improvement that these materials bring is that they are insoluble and the consistency of the paste does not change when immersed in the petroleum product, thus providing a sharp color change of the paste when placed on the gauge. The preferred materials for the whitener are titanium oxide, zinc oxide and certain grades of bentonite. In particular, titanium oxide is preferred because it is the most widely used white pigment because of its brightness and very high refractive index (n=2.4). Titanium oxide is also an effective opacifier in powder form, where it is employed as a pigment to provide whiteness and opacity to products. Titanium Oxide is widely used in the food, cosmetics and pharmaceutical industries. The inorganic oxide is employed in a concentration ranging from 19 to 21 percent of weight for best results. Those of ordinary skill in the art will recognize that any inorganic material meeting the aforementioned specifications can be used in the composition of the present invention.

As a filler, and for improvement of the cut between the colors when the paste is used, earth minerals in powder forms can be used, such as calcium sulfate, bentonite, or talc (hydrated magnesium silicate). It is preferred that sulfates be used, and in particular calcium sulfate hydrate, and/or talc in any ratio. Next the filler material is added to the mixture. The purpose of the filler material is not only to achieve the proper consistency of the paste, but also to ensure a sharp, distinctive cut line between the colors when used in the process of gauging. In addition, the filler functions to provide good absorbency for hydrocarbon liquid mixtures. Although a variety of inorganic powders can be used as fillers (talcum, bentonites, calcium carbonate), talc and/or calcium sulfate is the preferred filler because it provides a visual paste indicating composition meeting the above-specified object of the invention. The visual indicating paste of the present invention is odorless or with a slight lard smell with a smooth consistency and pleasant touch since most of the components are widely used in the food and cosmetics industries.

Talc and calcium sulfate are very common laboratory, industrial chemicals used in the food, cosmetics, and pharmaceutical industries. The filler is employed in a concentration ranging from 24 to 26% of weight for best results. Those of ordinary skill in the art will recognize that any inorganic material meeting the aforementioned specifications is employable in the compositions of the invention In use, a thin, uniform layer of visual indicating paste is spread on a measuring probe or gauge such as a stick. The stick with the paste thereon is introduced into a storage container. When the paste contacts the petroleum products in the container it changes color, usually in less than ten seconds, from a very light shade initially to a much darker shade of the same color. A sharp change in color will be present in the paste on the probe up to the point of the top level of the petroleum product in the container. The sharp division between the light and dark colors ensures an accurate reading of the level of petroleum products in the container indicated on the measuring probe.

The change in color of the visual indicating paste is due to the solubility properties of the non-polar dyes. The solubility of the non-polar dyes in hydrocarbon mixtures increases with the decrease of the molecular weight of the hydrocarbon mixtures. When the liquid product touches the paste, the dye dissolves quickly into the fuel, which is readily absorbed by the filler (calcium sulfate and/or talc) providing a very sharp visual color change on the paste. The paste will not bleed or run off the measuring probe when contacted with the liquid hydrocarbon mixtures (petroleum products).

The composition of the present invention may be manufactured by customary mixing methods. In general, the components of the composition are conventionally fed into a mixer at ambient temperature and blended to an even, smooth texture. The preferred order of mixing the ingredients is to first incorporate the dye into the carrier, then the whitener and the filler.

The paste of the present invention is different because of the overall performance, long self life, reduced time of immersion (less than 10 s), not dissolving in the fuel, plus all its components are user and environmental friendly.

Those of ordinary skill in the art will recognize that many obvious modifications may be made thereto without departing from the spirit or scope of the present invention as set forth in the appended claims.

What is claimed is:

1. A composition for a visual indicating paste for detecting the level of hydrocarbon mixtures in storage containers consisting of:
    a. A non-polar dye mixed in the visual indicating paste that will change color from a light shade to a dark shade when contacted by the hydrocarbon mixtures;
    b. A high molecular weight carrier;
    c. A whitening agent comprising an inorganic oxide; and
    d. A filler material comprising an inorganic powder.

2. The composition of claim 1 wherein the non-polar dye is selected from one of the following: Solvent Red 19, Solvent Red 24, Solvent Red 149, Permalex Red 2B, Permalex Violet B, Sudan Orange, Sudan Red 380, Oil Red, Orcosolve Red, Solvent Green 33, Permalex Green 5B, Permalex Blue AP, Solvent Blue 35 and Orcosolve Oil Blue.

3. The composition of claim 1 wherein the non-polar dye comprises Orcosolve Blue.

4. The composition of claim 3 wherein the non-polar dye is present in a concentration of about 0.9 to 1.4 percent by weight.

5. The composition of claim 1 wherein the high molecular weight carrier comprises a mixture of animal fat and petrolatum in an approximate ratio of 5 to 1, wherein the animal fat is selected from the group consisting of lard, tallow, and mixtures thereof.

6. The composition of claim 5 wherein the high molecular weight carrier is present in a concentration of about 53 to 55 percent by weight.

7. The composition of claim 1 where the whitening agent is titanium oxide.

8. The composition of claim 7 wherein the whitening agent is present in a concentration of about 19 to 21 percent by weight.

9. The composition of claim 1 wherein the filler material comprises a mixture of talc and calcium sulfate in any ratio.

10. The composition of claim 9 wherein the filler material is present in a concentration of about 24 to 27 percent by weight.

* * * * *